(12) United States Patent
Llinas et al.

(10) Patent No.: US 8,315,686 B2
(45) Date of Patent: Nov. 20, 2012

(54) CORTICAL ELECTRODE ARRAY AND METHOD FOR STIMULATING AND RECORDING BRAIN ACTIVITY

(75) Inventors: Rodolfo R. Llinas, New York, NY (US); Mutsuyuki Sugimori, New York, NY (US)

(73) Assignee: New York University, New York, NY (US)

( * ) Notice: Subject to any disclaimer, the term of this patent is extended or adjusted under 35 U.S.C. 154(b) by 360 days.

(21) Appl. No.: 12/362,805

(22) Filed: Jan. 30, 2009

(65) Prior Publication Data

US 2009/0192569 A1 Jul. 30, 2009

Related U.S. Application Data

(60) Provisional application No. 61/024,823, filed on Jan. 30, 2008.

(51) Int. Cl.
*A61N 1/36* (2006.01)
(52) U.S. Cl. ............ 600/378; 607/36; 607/45; 607/115; 607/116; 607/155; 600/544
(58) Field of Classification Search ............ 607/36, 607/45, 155, 115, 116; 600/378, 544
See application file for complete search history.

(56) References Cited

U.S. PATENT DOCUMENTS

| | | | | |
|---|---|---|---|---|
| 4,328,813 A | * | 5/1982 | Ray | 607/139 |
| 4,903,702 A | * | 2/1990 | Putz | 600/377 |
| 5,843,150 A | * | 12/1998 | Dreessen et al. | 607/116 |
| 6,016,449 A | | 1/2000 | Fischell et al. | |
| 6,154,677 A | * | 11/2000 | Leysieffer | 607/61 |
| 6,480,743 B1 | | 11/2002 | Kirkpatrick et al. | |
| 7,006,859 B1 | * | 2/2006 | Osorio et al. | 600/378 |
| 7,302,298 B2 | | 11/2007 | Lowry et al. | |
| 2004/0006264 A1 | | 1/2004 | Mojarradi et al. | |
| 2004/0243205 A1 | | 12/2004 | Keravel et al. | |
| 2005/0075680 A1 | | 4/2005 | Lowry et al. | |
| 2006/0106430 A1 | | 5/2006 | Fowler et al. | |
| 2006/0190056 A1 | | 8/2006 | Fowler et al. | |
| 2007/0106143 A1 | | 5/2007 | Flaherty | |
| 2007/0255338 A1 | * | 11/2007 | Wahlstrand | 607/45 |
| 2007/0265489 A1 | | 11/2007 | Fowler et al. | |
| 2007/0288072 A1 | | 12/2007 | Pascual-Leone et al. | |
| 2008/0033503 A1 | | 2/2008 | Fowler et al. | |
| 2008/0039895 A1 | | 2/2008 | Fowler et al. | |
| 2008/0046035 A1 | | 2/2008 | Fowler et al. | |

OTHER PUBLICATIONS

K.S. Guillory et al., "Electode arrays for large-scale neural interfaces", Proceedings of the Second Joint EMBS/BMES Conference, IEEE, Oct. 23-26, 2002; p. 2060-2061.

* cited by examiner

*Primary Examiner* — Niketa Patel
*Assistant Examiner* — Alyssa M Alter
(74) *Attorney, Agent, or Firm* — Foley & Lardner LLP (57) ABSTRACT

An electrode device and a method of installing the electrode device in the vicinity of the brain. The electrode device includes a plurality of electrode assemblies, each with at least one electrode lead, extending from a common base. The base is configured to be positioned on an outside of the patient's cranium with each electrode assembly projecting individually through a hole in the patient's cranium such that the electrode lead is in the vicinity of the brain. The method of installation includes carving a recess out of the patient's cranium and inserting the base therein. Each of the electrode assemblies are placed in their respective holes in order to stimulate, monitor or record neurological activity. The electrode device may be used over long periods of time for chronic treatment or recording.

20 Claims, 5 Drawing Sheets

CORTICAL ELECTRODE ARRAY AND METHOD FOR STIMULATING AND RECORDING BRAIN ACTIVITY

CROSS REFERENCE TO RELATED APPLICATIONS

The present invention claims the benefit of U.S. Provisional Patent Application Ser. No. 61/024,823, filed on Jan. 30, 2009, the contents of which are hereby incorporated by reference in their entirety.

FIELD OF THE INVENTION

The present invention relates to an electrode array for use with the brain, and specifically relates to a cortical electrode array and methods of its installation and use in a human.

BACKGROUND

A variety of therapies and analysis of the brain may be performed using electrodes placed in direct contact with brain tissue, in contact with the dura mater surrounding the brain, or in the vicinity of the brain. The electrodes may be used for stimulation, such as therapies for treating the tremor associated with Parkinson's disease, dystonia, central pain, tinnitus and other thalamo-cortical dysrhythmias such as OCD (obsessive compulsive disorder), schizoaffective disorders and manic/depressive syndrome. Alternatively, the electrodes may be used to monitor and record neurological activity in the brain. Recording brain activity can be useful in analyzing and treating abnormal neurological activity or diseases. Likewise, immediate monitoring of activity in the brain can potentially be used to control prosthetics.

One use of biomedical electrodes with the brain is carried out by drilling a hole in the cranium and inserting an electrode assembly into the patient's head to contact the brain tissue or dura mater surrounding the brain. The electrode assembly may include more than one electrode lead thereon. However, all of the electrode leads are typically placed along the length of the electrode assembly, which is typically tube-shaped. Thus, the positioning of the electrodes on this type of electrode assembly is limited. For deep brain stimulation, the electrodes are typically inserted relatively deep into the brain in order to contact particular areas of interest. As a result, deep brain stimulation is somewhat invasive, and may lead to complications such as bleeding.

For long-term chronic therapies and analysis, a biomedical electrode device can be implanted inside the patient's cranium. The implanted electrode can be used to stimulate or monitor neurological activity over long periods of time. However, implanting an electrode array inside a patient's head requires a large craniotomy. This type of surgical procedure is intensive, involves health risks and includes an extended healing time.

Thus, there is a need for a device and a method of installing the device that can stimulate and/or monitor neurological activity at a variety of locations in the brain without requiring an extensive craniotomy or the removal of a portion of the cranium.

SUMMARY

The present invention provides a cortical electrode device that includes an array of electrode assemblies, each of which individually penetrates through a separate small hole in the cranium. A base for the array of electrode assemblies is disposed on the outside of the cranium. Each electrode assembly includes an electrode lead either in direct contact or in the vicinity of tissue inside the patient's cranium such as brain tissue or dura mater. The cortical electrode device is particularly well suited to provide cortex stimulation, which in comparison with deep brain stimulation, is less invasive. The cortical electrode device can be configured to stimulate activity in the brain, monitor activity, or both stimulate and monitor activity. The device may also record any activity that it monitors. If the electrode device is configured to both stimulate and monitor neurological activity, each electrode assembly can include a stimulating electrode lead and a monitoring electrode lead. Alternatively, the electrode device may include a number of stimulating electrode assemblies that are dedicated to stimulating neurological activity and a number of monitoring electrode assemblies that are dedicated to monitoring neurological activity.

The invention also provides a method of installing the electrode device in a patient. The method includes opening a small section of scalp to expose a portion of the surface of the patient's cranium. A recess, crevice, depression, cavity, indented area, fossa or similar space adapted to receive the electrode device is carved out of the surface of the patient's cranium, for example, by drilling the bone to remove portions thereof. The machining of the patient's skull may be performed by a robot drill mounted on a head holder to avoid any human error or variation. Alternatively, the recess may be formed manually, for example, by using a template or other guide mounted to the skull to show the positioning of the recess, and optionally, the positioning of the individual holes to be drilled. The recess may include a first space to accommodate the base of the electrode assembly array. A second space may also be machined out of the cranium as part of the recess. The second space may accommodate the electrical leads of the electrode assemblies.

The method also includes boring a number of holes through the cranium to the inside of the patient's head. The holes may be positioned such that they are aligned with the recess and with the electrodes in the array. In other words, the holes may be disposed to provide an opening between the inside of the cranium and the bottom of the recess. The holes may be drilled using automated or programmable equipment, or manually drilled using a template or a guide. Each electrode assembly may be positioned and implanted through the hole matrix bored through the cranium such that the electrode tips contact or are in the vicinity of the brain tissue. In one embodiment of the method, the electrode leads may be positioned to rest on the surface of the dura mater that surrounds the patient's brain. The base of the electrode array is placed in the first space of the recess. Accordingly, an outer side of the base of the electrode array may be positioned flush with an outer surface of the cranium.

In accordance with this installation method, the electrode device can be discreetly placed in a patient's head. To further obscure the electrode device, the section of scalp may be replaced over the base of the electrode array. As a further advantage, by having the electrode device securely placed within the area normally occupied by the cranium, the electrode device is protected. First, the exposure of the electrode device is reduced because it is sunken into the recess formed in the cranium and is therefore less vulnerable to damage. Second, the patient will be less likely to accidentally damage the electrode device due to misjudging the device's location or forgetting to be conscious of its placement.

As a result of the discreet location of the electrode device on the patient's cranium, both with respect to appearance and safety, the electrode device is well suited for long term use.

Thus, the electrode device can be implanted in the patient's cranium and held in that location over long periods of time. The electrode device is therefore suitable for extended treatment with electrode stimulation or with chronic monitoring and recording of neural activity. An additional advantage of the device and the method of installation is that the long usage life of the electrode device also allows periodic stimulation therapy and long term monitoring of the therapy's effects. In other words, periodic stimulation can be carried out under the instruction of medical personnel and the brain activity can be monitored and/or recorded in response. This allows not only the immediate response of the brain activity to be monitored, but also the monitoring of the long term response of the brain activity to any treatment thereof.

BRIEF DESCRIPTION OF THE FIGURES

The present invention will be described in the following with respect to exemplary embodiments and the drawings, in which.

DETAILED DESCRIPTION

Figure 1:
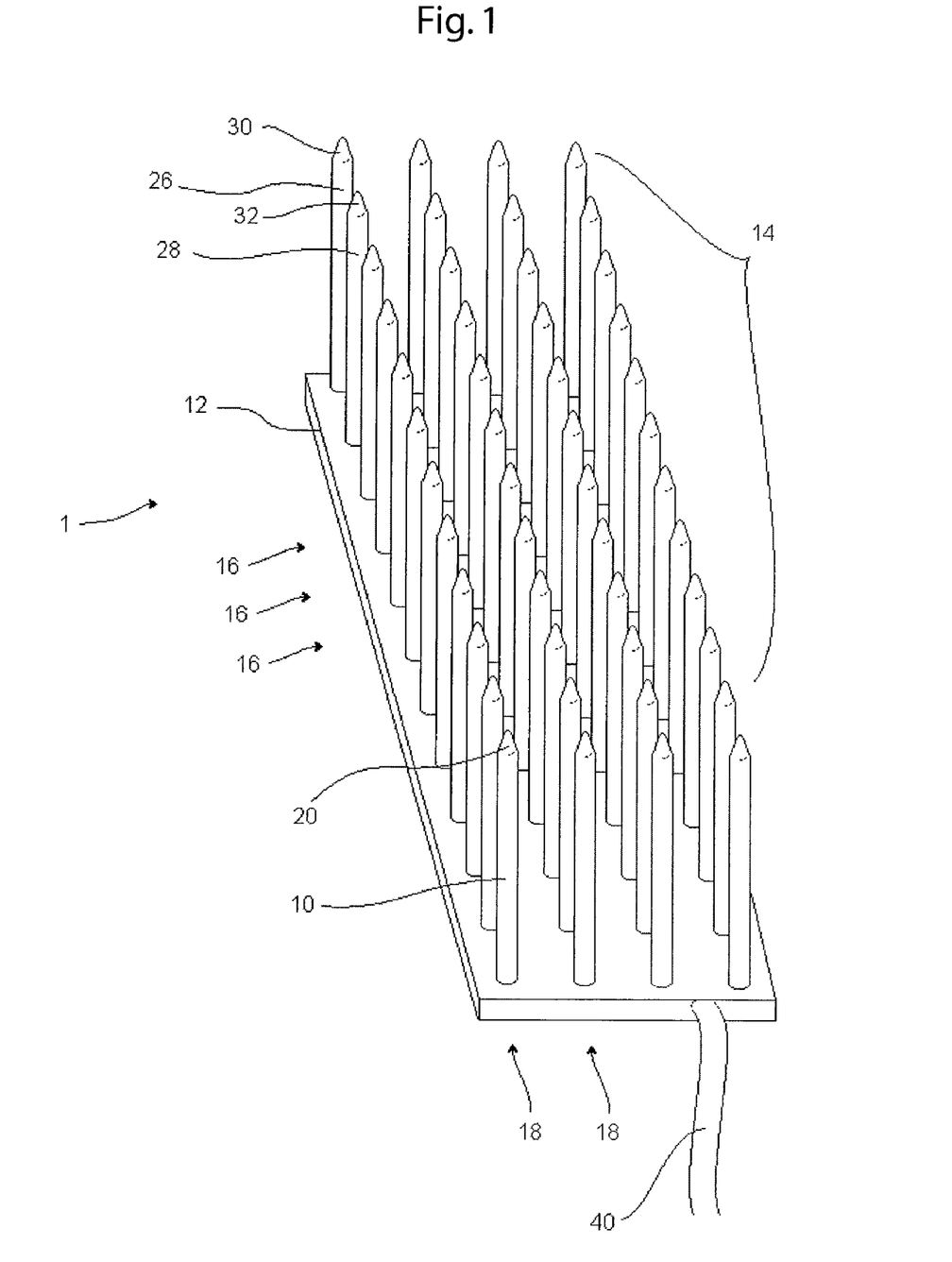
FIG. 1 is a perspective view of an embodiment of an electrode device in accordance with the invention.

FIG. 1 shows an electrode device 1 configured to carry out neuromodulation either in the form of stimulating or monitoring/recording neurological activity. The electrode device 1 includes a plurality of electrode assemblies 10 extending from a base 12 of the device. The assemblies 10 may be arranged in an array, as shown, and the electrode array 14 can include a plurality of rows 16 and a plurality of columns 18 of electrode assemblies in a regular pattern, as shown in FIG. 1. In an exemplary embodiment, the electrode assemblies may each be on the order of 1.5 mm in diameter, and spaced 5 mm center to center. Alternatively, the electrode assemblies can be arranged on the base 12 of the electrode device in a specific pattern as determined by their desired placement with respect to the brain or dura mater. Also, as shown in FIG. 1, the length of each electrode assembly 10 may be the same. For example, in one embodiment of the electrode device 1, the electrode assemblies 10 are configured to rest on the dura mater surrounding the brain. In this case, each of the electrode assemblies 10 may be the appropriate length to pass through the patient's cranium and rest close to the dura mater. Alternatively, the electrode assemblies 10 can be configured to penetrate into the brain tissue to precise locations within the brain. In this instance, it may be advantageous to have the electrode assemblies 10 have a variety of lengths. Of course, due to geometric constraints, it may be advantageous to have electrode assemblies 10 of various lengths even when they are configured to rest on the dura mater, for instance, if there is variation in the depth of the dura mater with respect to the outside of the cranium. Indeed, the actual exact anatomy of the cranium with thickness determinations and distances between the inner cranial table and the dura mater may be determined using MRI imaging prior to surgery.

Figure 3:
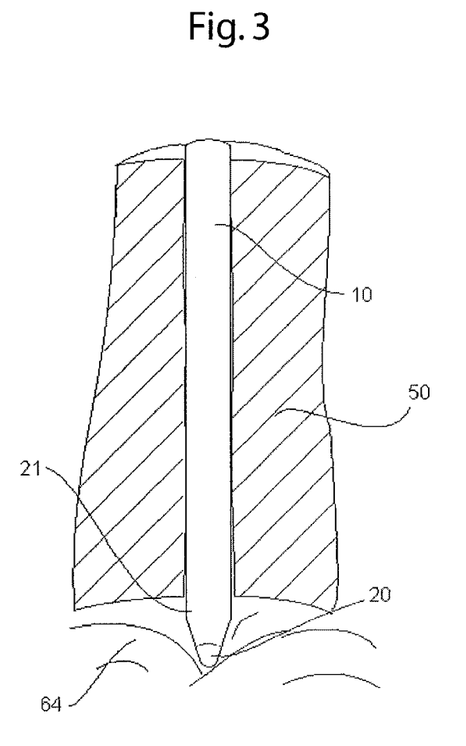
FIG. 3 is a cross section view showing an embodiment of an electrode assembly in accordance with the invention.
Figure 4:
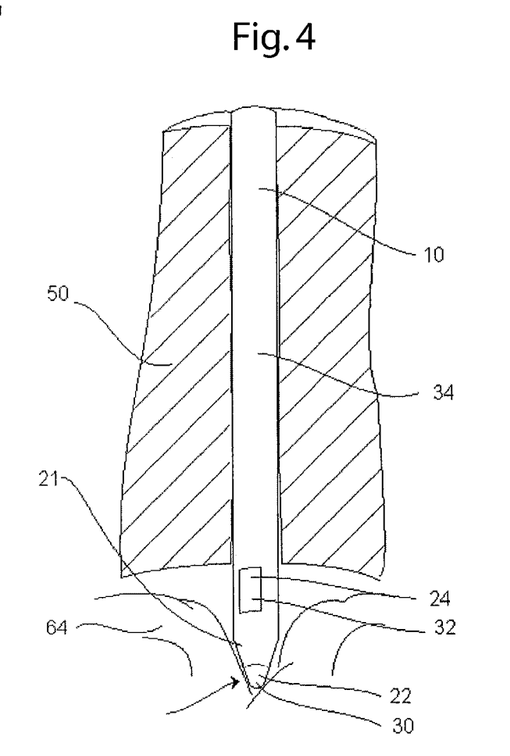
FIG. 4 is a cross section view showing another embodiment of an electrode assembly in accordance with the invention.

Each electrode assembly 10 used in the electrode device 1 of the present invention may be as simple as a unitary rigid conductive element that is configured to stimulate or monitor neurological activity. The entirety of each electrode assembly 10 may serve as a single electrode lead 20. In such a case, the cranium itself is relied upon to insulate the electrode assemblies 10 in the array 14 from one another. Alternatively, as shown in FIGS. 3 and 4, each electrode assembly 10 may include an insulating sleeve or outer wall 21 that insulates the electrode assemblies 10 in the array 14 from each other. At least one electrode lead 20 may be exposed on the surface of the electrode assembly 10. As shown in FIG. 4, the electrode assemblies 10 in the device 1 may include multiple electrode leads 20, such as first lead 22 and second lead 24.

In a simple embodiment of the electrode device 1, each electrode assembly 10 may include one electrode lead 20 and all of the electrode leads 20 may be configured to carry out one form of neuromodulation. In other words, all of the electrode assemblies can be stimulating electrode assemblies 26 each with a stimulating electrode lead 30, or the electrode assemblies 10 can be monitoring electrode assemblies 28 each with a monitoring electrode lead 32.

In a more complex embodiment of the electrode device 1, the device 1 can be configured to perform both stimulating and monitoring activity by including both stimulating electrode leads 30 and monitoring electrode leads 32. If the electrode assemblies 10 only include a first electrode lead 22, each electrode assembly 10 may be confined to a single function. Thus, the electrode assembly 10 may be either a stimulating electrode assembly 26 or a monitoring electrode assembly 28. The electrode device 1 can be configured with stimulating electrode assemblies 26 and monitoring electrode assemblies 28 dispersed throughout the array. For instance, the electrode device 1, shown in FIG. 1, which includes forty-eight electrode assemblies, may have twenty-four stimulating assemblies 26 and twenty-four monitoring assemblies 28.

In another embodiment, one or more of the electrode assemblies 10 included in the electrode device can perform two different functions. For instance, it may be possible that a single electrode lead 20 can be configured to both stimulate activity and monitor activity in accordance with the performance of a recording/stimulating system. For example, the electrode lead 20 could be switched over time between stimulating and monitoring or recording.

In an embodiment with multi-functioning electrode assemblies 34, these electrode assemblies may include two electrode leads 20 that perform different functions. As shown in FIG. 4 and mentioned above, the electrode assembly 10 may include both first and second electrode leads 22, 24, each of which can be configured to perform a different function, such that the electrode assembly 10 is a multi-function electrode assembly 34. Accordingly, the first electrode lead 22 may be a stimulating electrode lead 30 while the second electrode lead 24 may be a monitoring electrode lead 32. Of course, the first and second electrode leads may be configured to perform the same function. The first electrode lead 22 may be positioned on a distal tip of the electrode assembly 34, while the second electrode lead 24 may be positioned on a side of the assembly 34.

If the electrode device 1 includes multi-functioning electrode assemblies 34, they can be included throughout the entire array. Alternatively, in one embodiment of the device 1 only specific electrode assemblies 10 in the array 14 are configured as multi-functioning electrode assemblies 34, while the remaining electrode assemblies 10 are single function electrode assemblies.

As stated above, each of the electrode assemblies 10 is connected to a base 12 which holds the electrode assemblies in their respective position and helps accurately position the electrode leads 20 on the targeted area, for example of dura mater. In its simplest form, the base 12 acts as a support for the electrode assemblies 10, ensuring that they are maintained at a distance from one another. In this embodiment the electrode assemblies 10 may pass through the base 12 and have an individual conductive element attached thereto. The conductive element is connected to a simulating/recording system that electrically operates the specific electrode assembly 10. The base 12 of the electrode device can be either rigid or flexible, each having its own advantages. A rigid base 12 is capable of very securely positioning the electrode assemblies 10 and maintaining their respective distances from each other. On the other hand, a flexible base 12 may more easily fit with the contour of the patient's cranium.

A more complex embodiment of the base 12, may include electrical circuitry therein. This circuitry may be used to interface the electrical leads of the electrode assemblies such that the conductive element for each device can be linked to the stimulating/recording system through a connection 40. In one embodiment, the base may include an electronic controller to control the behavior of the electrodes or a data storage device to store signals recorded with monitoring electrode leads.

Figure 2:
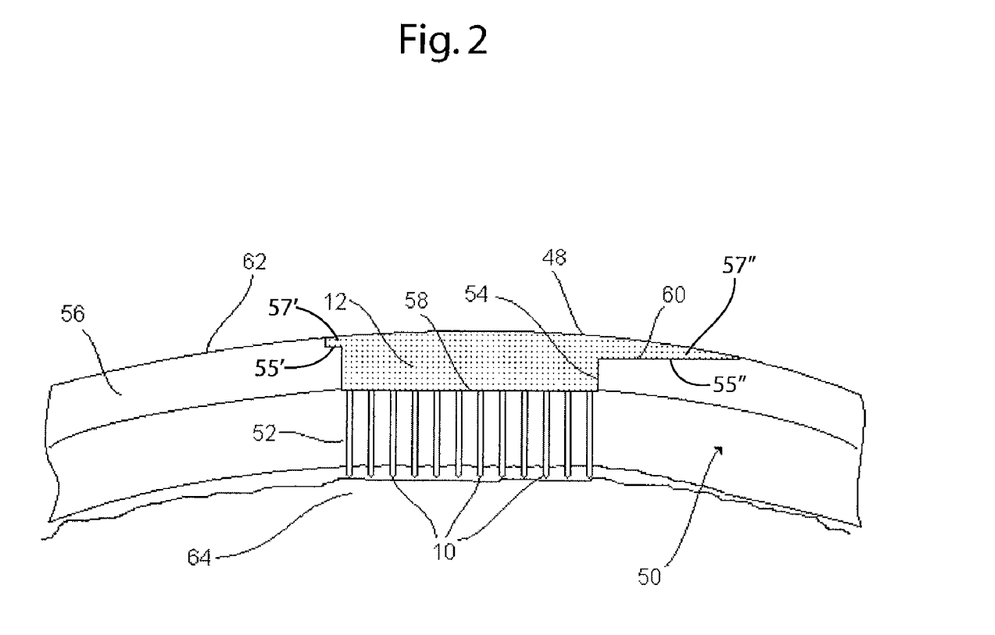
FIG. 2 is a cross section view showing the device of FIG. 1 implanted in the cranium of a patient.

The electrode device 1 is configured such that the base 12 is located on the outside of the cranium 50, as shown in FIG. 2. In order to communicate with the brain, each of the electrode assemblies 10 passes through an individual hole 52 that is bored through the cranium 50. The base 12 itself can be disposed in a recess 54 formed in the cranium 50. For example, the recess 54 may be carved out of the outer lamella 56 of the cranium 50 and shaped specifically to accommodate the base 12. The recess 54 can also include a first space 58 designed to accommodate the base 12 and a second space 60 designed to accommodate a portion of the connection 40 to the stimulating/recording system. The recess 54 can also optionally be provided with lips 55', 55" which are shaped to correspond to matching extensions 57', 57" on the base 12 in order to provide proper registration and maintain positioning between the base 12 and the cranium 50. The electrode device 1 illustrated in FIG. 2 is shown as having a flat base 12; however, alternatively, the base 12 may be curved to match the corresponding curvature of the cranium where the electrode device 1 is to be installed. When a flat base is used, the lengths of the individual electrodes may be modified to compensate for curvature of the cranium, such that in an installed position, the tips of the electrodes extend to a uniform level relative to the cranium 50.

The method of preparing the patient and installing the electrode device 1 may be carried out in a variety of different ways or sequences and avoids the necessity of a craniotomy. Before the electrode device has access to the brain, the cranium must be operated on to provide an access path. The work on the cranium 50 includes carving a recess 54 in the cranium next to its outer surface 62. Additionally, a hole 52 is bored through the entirety of the cranium 50 for each electrode assembly 10. The electrode assemblies 10 are then placed through the holes 52 such that the electrode leads 20 rest on a surface of the dura mater 64 or penetrate the brain tissue with the base positioned in the recess 54. These steps may be carried out using automated or programmable equipment, or alternatively may be carried out manually using a template, guide or other mechanism for assisting in the preparation of the cranium.

As stated above, the method can be carried out in a variety of different ways or sequences and each may have certain advantages. The specific embodiments discussed herein are merely exemplary. In one embodiment, the work on the cranium 50 may be carried out by first carving out the recess 54 and then boring the holes 52. In this approach, the boring depth is reduced because of the prior removal of the lamella 56. On the other hand, boring of the cranium 56 may be simpler and less dangerous when the full thickness of the cranium 56 is still intact. Thus, it may be advantageous to first bore the holes 52 and then carve out the recess 54. The electrode device 1 may be installed after the cranium has been reshaped. The electrode device 1 can be installed as a pre-assembled device such that the electrode assemblies 10 and the base 12 are inserted into the respective holes 52 and recess 54 at substantially the same time. An adhesive or filler may then be applied to hold the electrode device in place. Alternatively, bolts or a mechanical element may be used to hold the electrode device in place. Instead of installing the device 1 all at once, the device may be assembled and installed in place on the cranium 50. For instance, the electrode assemblies 10 may each be inserted through its respective hole 52 in the cranium and the base subsequently attached thereto. This latter approach provides the advantage of allowing more precise and individualized placement of the electrode assemblies 10. Further, it allows each electrode assembly to be affixed to the cranium individually, and each hole may be filled with a filler or adhesive individually.

Instead of performing all the operations on the cranium 50 at once, in one embodiment the assembly of the electrode device 1 may be carried out as the device 1 is assembled. For instance, the recess 54 could first be carved out of the cranium and subsequently the base could be inserted and fixed in the recess 54. The holes 52 could then be precisely bored based on their placement with respect to the base 12. Finally, the electrode assemblies 10 could be inserted through the holes 52 and fixed in the base 12. Other sequences of the method steps of the invention could produce foreseeable advantages and the present invention is not limited to any specific order. Also, once the recess 54 is formed, a mold may be made and then used to create a base which fits precisely within the recess.

With the present invention, the electrode device can be installed without a craniotomy. Also if the electrode is to be permanently removed, the inner table of the cranium not having been removed will promptly obliterate the small perforations required for electrode access to the dural surface. Accordingly, important and life-altering therapy, or potentially life-altering analysis can be carried out on a patient without this risky surgery. In addition, with certain embodiments of the invention the electrode device can be installed such that the outer surface 48 of the base 12 is flush with the outer surface of the patient's cranium 50. As a result the electrode device can be discreet. Further, the electrode device is less vulnerable to damage than if it were exposed as a protrusion on patient's head. Further still, if the outer surface 48 is flush with the patient's head, the patient will be less likely to damage it because he will inherently protect the device as he would his own head. In other words, if the device protrudes, the patient may forget or misjudge its location and accidentally bump the device. In contrast, if the device is flush with the patient's head, he is no more likely to bump the device than he would his own head.

Figure 5:
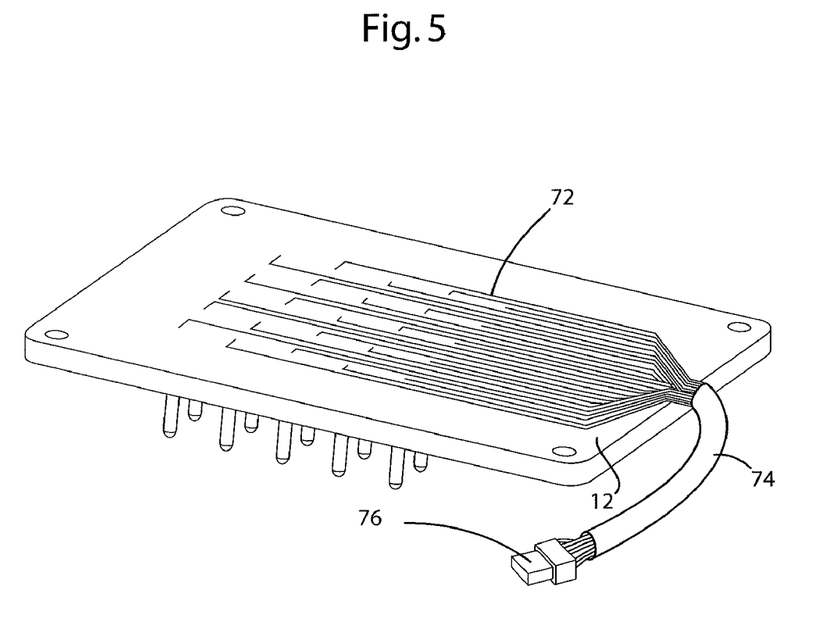
FIG. 5 is a perspective view of an embodiment of the electrode device showing conductive traces.
Figure 6:
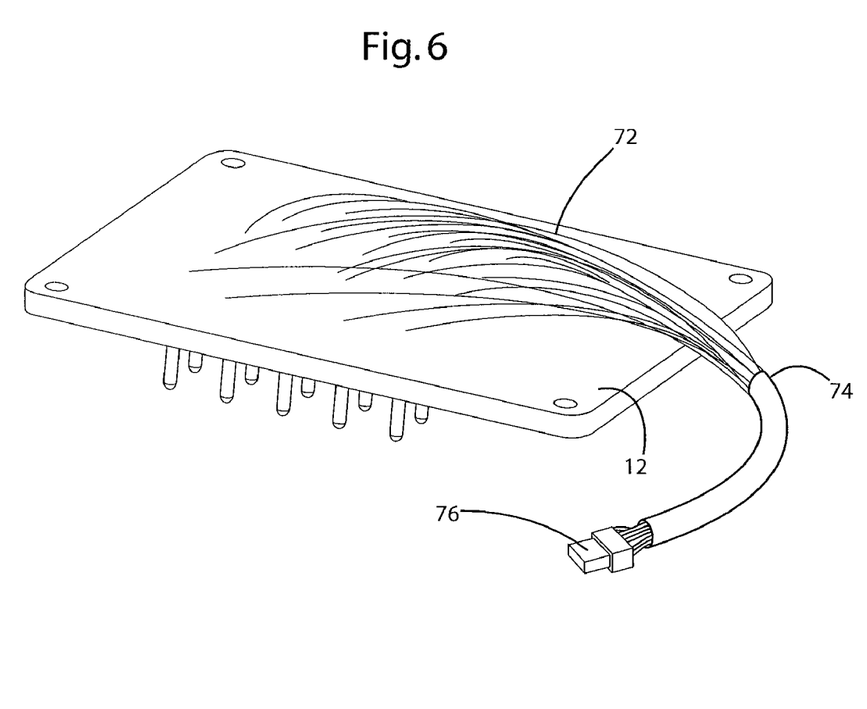
FIG. 6 is a perspective view of an embodiment of the electrode device showing individual conductors.

The electrode device provides an electrical or electromagnetic interface for communication between the individual electrodes and external electronic equipment. This interface may be, for example, in the form of conductive traces 72 on the base 12 (FIG. 5) providing electrical contact to each electrode, or alternatively, individual wires 74 (FIG. 6) which provide the electrical contact to each electrode. The conductive traces 72 or wires 74 interconnect with an interface such as a cable or connector 76 for further connection to external electronics.

Figure 7:
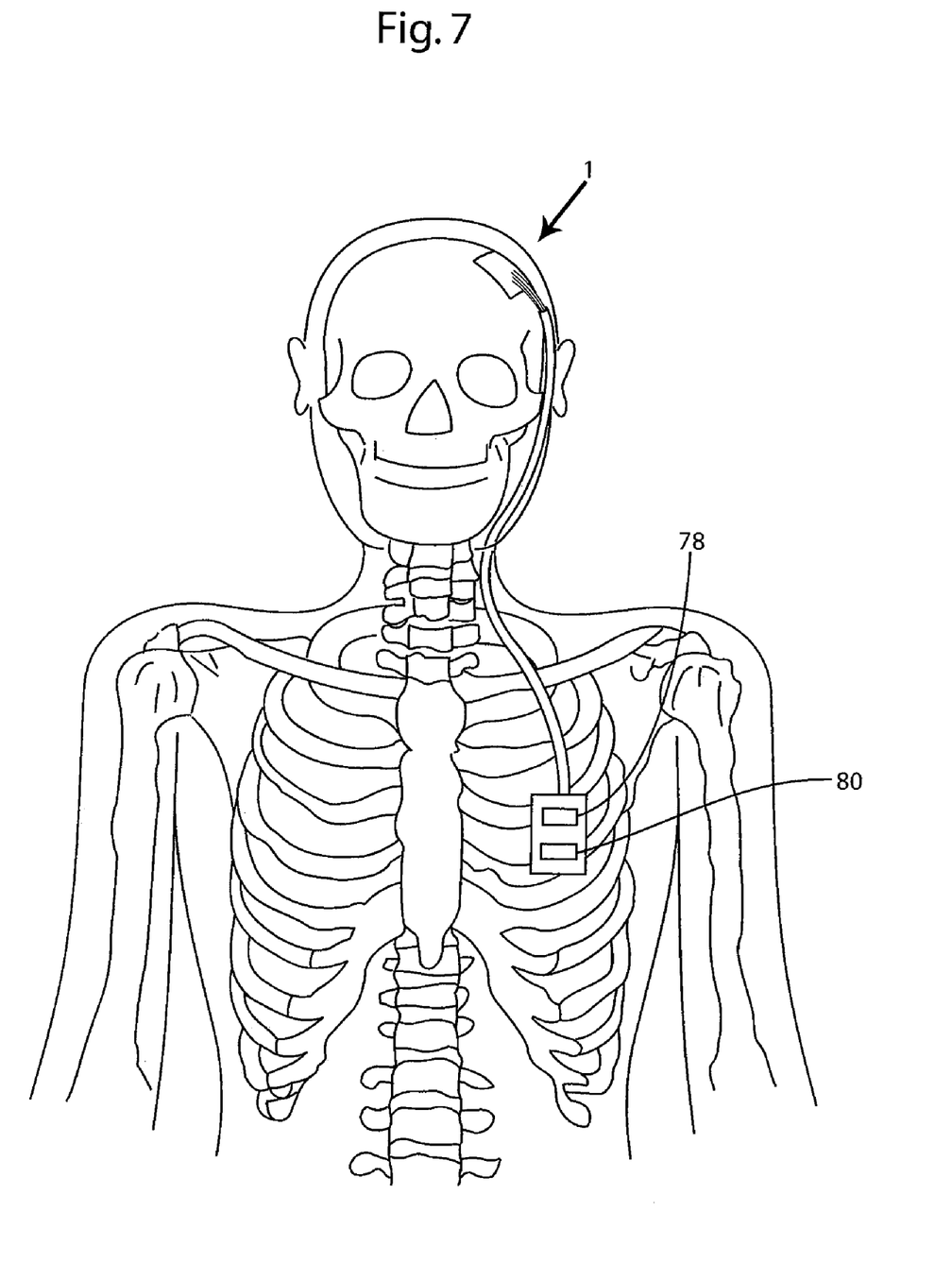
FIG. 7 is an illustration of a patient showing the positioning of the electrode device and associated electronics.

In one embodiment, the cable or connector 76 interfaces with wires positioned under the skin and extending into the patient's chest, where a power source 78 and communications interface 80 are implanted in a housing (FIG. 7). The power source 78 may be in the form of a battery, energizable coil, or the like, for providing electrical power for use with the electrode array. The communications interface 80 may be in the form of infrared, radiofrequency, or other electromagnetic interface for providing communication between external electronics and the electrode array. Alternatively, the communications interface 80 may be provided at the patient's cranium by way of a connector provided in the vicinity of the electrode array.

The electrode array of the present invention may be used, for example, to apply electrical signals to specific portions of the brain. The particular type of signals (e.g., amplitude, duration, frequency) may be determined based on an evaluation of the particular patient's condition and needs. Alternatively, the present invention may be used in connection with real-time monitoring and analysis of the patient's brain activity via the electrodes, which in turn is used to modify or adjust the particular signals applied via the electrodes.

Due to the foregoing advantages, the electrode device can be installed to provide chronic treatment and/or analysis of a patient's neurological activity. Thus, one aspect of the invention is the treatment of a patient with electrode stimulation followed by short term monitoring of the neurological activity as well as long term recording of the activity. By recording the brain activity over long periods of time, the patient's long term reaction to the stimulation treatment can be analyzed. This may allow future treatments to be more effective.

Although the invention has been described with respect to specific embodiments, it is to be understood that the invention is not limited by the specific embodiments described herein.

What is claimed:

1. An electrode array assembly for providing electrical communication with tissue including dura mater which is within a cranium having a thickness, a recess therein, a layer of the cranium, a plurality of through holes in the cranium and an outer lamella layer of the cranium, the assembly comprising:
 a base having an outer surface and having a structure enabling the base to be received in the recess formed in the cranium, the recess having a shape which is complementary to the base and a depth for the base which is less than the thickness of the cranium such that the layer of the cranium is provided between the base and the tissue and the outer surface of the base having a smooth transition with the outer lamella layer exposed to an environment outside the cranium;
 a plurality of electrode assemblies mounted directly underneath and to the base, each electrode assembly mounted at a respective first end to the base and extending in a generally outward direction away from the base toward a respective second end, each individual one of the electrode assemblies having a structure to be received within a respective one of the plurality of through holes in the layer of the cranium provided between the base and the tissue, thereby providing a substantial fit for each of the electrode assemblies to the respective one of the plurality of through holes and each electrode assembly including a conductive element for providing electrical communication between a respective portion of the tissue and a respective electrical conductor associated with the base and corresponding to the respective electrode assembly.

2. The electrode array assembly of claim 1, wherein the plurality of electrode assemblies are disposed in an array including a plurality of rows and a plurality of columns.

3. The electrode array assembly of claim 1, wherein the second end of the at least one of the plurality of electrode assemblies is configured to rest in a vicinity of the dura mater of the patient.

4. The electrode array assembly of claim 1, wherein at least one of the plurality of electrode assemblies is configured to penetrate into the brain tissue.

5. The electrode array assembly of claim 1, wherein at least one of the plurality of electrode assemblies includes a stimulating electrode lead.

6. The electrode array assembly of claim 1, wherein at least one of the electrode assemblies includes a monitoring electrode lead.

7. The electrode array assembly of claim 1, where at least one of the plurality of electrode assemblies includes more than one electrode lead.

8. The electrode array assembly of claim 1 further comprising a recording system configured to record electrical communication monitored by at least one of the plurality of electrode assemblies.

9. The electrode array assembly of claim 1 further comprising a communications interface connected to the plurality of electrode assemblies and configured to communicate at least one of electrical communications monitored by the electrode assemblies and stimulating activity to be carried out by the electrode assemblies.

10. The electrode array assembly of claim 9 for use in a chest of a patient wherein the communications interface is disposed in a housing, the housing configured to receive a power source and configured to be disposed in the chest of the patient.

11. The electrode array assembly as defined in claim 1 wherein an outer surface of the base is substantially flush with an outer surface of the patient's cranium.

12. A method of treating a patient with an electrode array assembly for providing electrical communication with tissue including dura mater inside the patient's cranium having a recess with a plurality of through holes and an outer lamella layer, the method comprising:
 providing an electrode array assembly including a base with an outer surface and a plurality of electrode assemblies mounted directly underneath and to the base, each electrode assembly having a first end adjacent the base and extending in a generally outward direction away from underneath the base to a respective second end, and each electrode assembly including a conductive element;
 forming a recess in an outer surface of the patient's cranium, the recess having a shape complementary to the base and a depth which is less than a thickness of the cranium such that a recessed portion of the cranium is provided within the recess and the outer surface of the base having a smooth transition with the outer lamella layer of the patient's cranium exposed to an environment outside the cranium;

boring a plurality of the through holes through the recess of the cranium;

inserting the base into the recess;

disposing each electrode assembly in a respective one of the plurality of the through holes in the recess of the cranium such that the second end of each electrode assembly is disposed in a vicinity of a respective portion of the tissue and each electrode of the electrode assembly having a substantial fit and complementary shape for the respective one of the plurality of through holes which receives each of the electrodes; and conducting electrical communication between the conductive element of each electrode assembly and the tissue.

13. The method of claim 12, wherein the second end of at least one of the plurality of electrode assemblies penetrates the brain tissue and the respective portion of the tissue includes the brain tissue.

14. The method of claim 12, wherein the electrical communication includes monitoring activity of the patient's brain.

15. The method of claim 14, further comprising providing a recording system in communication with the electrode array assembly, and recording the monitored activity of the patient's brain.

16. The method of claim 12 wherein the electrical communication includes stimulating the patient's brain.

17. The method of claim 12, further comprising providing a communications interface in communication with each conductive element, and providing communications between the electrode array assembly and an external electronic device through the communications interface.

18. The method of claim 12 wherein the recess is formed in the outer lamella of the patient's cranium.

19. The method of claim 12 further comprising fixing the base of the electrode array assembly in the recess.

20. The method of claim 12 wherein an outer surface of the base is substantially flush with an outer surface of the patient's cranium.

* * * * *

UNITED STATES PATENT AND TRADEMARK OFFICE
CERTIFICATE OF CORRECTION

PATENT NO. : 8,315,686 B2
APPLICATION NO. : 12/362805
DATED : November 20, 2012
INVENTOR(S) : Rodolfo R. Llinas and Mutsuyuki Sugimori Page 1 of 1

It is certified that error appears in the above-identified patent and that said Letters Patent is hereby corrected as shown below:

In the Specification

Column 1, following after the "Cross Reference to Related Applications" sub-heading and paragraph, add new sub-heading and paragraph:
STATEMENT OF GOVERNMENT INTEREST
"This invention was made with government support under grant number CTS0227589 awarded by the National Science Foundation. The government has certain rights in the invention."

Signed and Sealed this
Nineteenth Day of August, 2025

Coke Morgan Stewart
*Acting Director of the United States Patent and Trademark Office*